US008623631B2

(12) United States Patent
Endo et al.

(10) Patent No.: US 8,623,631 B2
(45) Date of Patent: Jan. 7, 2014

(54) MODIFIED PROMOTER

(75) Inventors: Keiji Endo, Haga-gun (JP); Katsuya Ozaki, Haga-gun (JP)

(73) Assignee: Kao Corporation, Tokyo (JP)

( * ) Notice: Subject to any disclaimer, the term of this patent is extended or adjusted under 35 U.S.C. 154(b) by 1294 days.

(21) Appl. No.: 10/589,960

(22) PCT Filed: Mar. 4, 2005

(86) PCT No.: PCT/JP2005/003757
§ 371 (c)(1),
(2), (4) Date: Aug. 18, 2006

(87) PCT Pub. No.: WO2005/085441
PCT Pub. Date: Sep. 15, 2005

(65) Prior Publication Data
US 2008/0014608 A1 Jan. 17, 2008

(30) Foreign Application Priority Data
Mar. 5, 2004 (JP) .................................. 2004-062853

(51) Int. Cl.
*C12N 1/20* (2006.01)
*C12P 21/00* (2006.01)
*C07H 21/04* (2006.01)
(52) U.S. Cl.
USPC ...................... 435/252.3; 435/71.2; 536/23.1
(58) Field of Classification Search
None
See application file for complete search history.

(56) References Cited

FOREIGN PATENT DOCUMENTS

JP 200 210081 8/2000
JP 2003 47490 2/2003

OTHER PUBLICATIONS

Sumitomo, N. et al.,"Application of the upstream region of a *Bacillus* endoglucanase gene to high-level expression of foreign genes in *Bacillus subtilis*" Biosci. Biotechnol. Biochem., vol. 59, No. 11, pp. 2172-2175, 1995.
Wang, PZ. et al., "Overlapping promoters transcribed by *Bacillus subtilis* sigma 55 and sigma 37 RNA polymerase holoenzymes during growth and stationary phases" J. Biol. Chem., vol. 259, No. 13, pp. 8619-8625, Jul. 10, 1984.
Sumitomo, N. et al.,"Nucleotide sequence of the gene for an alkaline endoglucanase from an alkalophilic *Bacillus* and its expression in *Escherichia coli* and *Bacillus subtilis*", Biosci. Biotechnol. Biochem., vol. 56, No. 6, pp. 872-877, 1992.
Eichenberger, P. et al.,"The sigmaE regulon and the identification of additional sporulation genes in *Bacillus subtilis*" J. Mol. Biol., vol. 327, No. 5. pp. 945-972, Apr. 2003.
Ju,J. et al.,"Sigma factor displacement from RNA polymerase during *Bacillus subtilis* sporulation" J. Bacteriol., vol. 181, No. 16, pp. 4969-4977, Aug. 1999.
Hakamada Yoshihiro et al., "Deduced Amino Acid Sequence and Possible Catalytic Residues of a Thermostable, Alkaline Cellulase from an Alkalphilic *Bacillus* Strain," Bioscience Biotechnology and Biochemistry, vol. 64, No. 11, Nov. 2000, pp. 2281-2289, XP002435647, ISSN: 0916-8451.
Database EMBL, Dec. 15, 2000, "*Bacillus* sp. Gene for Cellulase, Complete Cds, Isolaet: KSM-S237," XP002439853, Retrieved from EBI Accession No. EMBL:AB018420, Database Accession No. AB018420.
Database EMBL, Feb. 8, 2002 "Thermostable Alkaline Cellulase Gene," XP002435652, Retrieved from EBI Accession No. EMBL:E37675, Database Accession No. E37675.
Database EMBL, Jun. 18, 2003, "Host Microorganisms," XP002435653, Retrieved from EBI Accession No. EMBL:BD186022, Database Accession No. BD186022.
Database EMBL, Mar. 16, 2001, "*Bacillus* sp. KSM-64 Alkaline Cellulase Gene Upstream Region," XP002435654, Retrieved from EBI Accession No. GSN:AAC87601Database Accession No. AAC87601.
Database EMBL, Apr. 19, 1990, "*Bacillus* sp. Cellulase Gene Complete cds, Clone pFK1," XP002439854, Retrieved from EMBL: M15743, Database Accession No. M15743.
Fukumori et al., "Molecular Cloning and Nucleotide Sequence of the Alkaline Cellulase Gene for the Alkalophilic *Bacillus* sp. Strain 1139," Journal of General Microbiology, Society for Microbiology, Reading, GB, vol. 132. (PT 8, Aug. 1986, pp. 2329-2335, XP002225732, ISSN: 0022-1287.
Kodama Takeko et al., Efefct of *Bacillus subtilis* spo0A Mutation on Cell Wall Lytic Enzymes and Extracellular Proteases, and Prevention of Cell Lysis, Journal of Bioscience and Bioengineering, vol. 103, No. 1, Jan. 2007, pp. 13-21, XP002435648, ISSN: 1389-1723.
Office Action issued Dec. 5, 2013 in Chinese Patent Application No. 200580007117.1 (with English-language translation).
John D. Helmann, et al., "RNA Polymerase and Sigma Factors", *Bacillus subtilis* and Its Closest Relatives: from Genes to Cells, 2002, pp. 289-312.
"The Search Report about the sigma A-typed promoter done in the database of transcriptional regulation in *Bacillus subtilis*", DBTBS, http://dbtbs.hgc.jp/, May 12, 2010, 13 pages.
A.O. Henriques, et al., "cse15, cse60, and csk22 Are New Members of Mother-Cell-Specific Sporulation Regulons in *Bacillus subtilis*", Journal of Bacteriology, vol. 179, No. 2, Jan. 1997, pp. 389-398.
"The result obtained by the searching of the sequence of Reference 3 using Genetyx-Win: Search Promoter Sequence", May 12, 2010, 3 pages.
"The promoters capable of recognizing sigE searched from the database of transcriptional regulation in *Bacillus subtilis* DBTBS", May 11, 2010, 1 page.

*Primary Examiner* — Nancy T Vogel
(74) *Attorney, Agent, or Firm* — Oblon, Spivak, McClelland, Maier & Neustadt, L.L.P.

(57) ABSTRACT

The present invention provides a modified promoter DNA capable of enhancing transcription of genes encoding proteins or polypeptides, and a method for producing proteins or polypeptides efficiently by use of the modified promoter DNA.
A promoter DNA recognized by SigA and SigE, which is produced by modifying a nucleotide sequence including a promoter recognized by SigA and bases in the vicinity thereof; an expression vector harboring the promoter DNA; a recombinant microorganism containing the expression vector; and a method for producing proteins or polypeptides characterized by culturing the recombinant microorganism.

34 Claims, 2 Drawing Sheets

DNA fragment to which a promoter sequence recognized by SigE has been introduced

MODIFIED PROMOTER

TECHNICAL FIELD

The present invention relates to a modified promoter DNA, an expression vector containing the DNA, a recombinant microorganism containing the expression vector, and a method for producing proteins or polypeptides through use of the recombinant microorganism.

BACKGROUND OF THE INVENTION

Microorganisms are widely used for industrially producing a broad range of useful substances, including alcoholic beverages, certain types of foods such as miso (i.e., fermented soybean paste) and shoyu (i.e., soy sauce), amino acids, organic acids, nucleic-acid-related substances, antibiotics, sugars, lipids, and proteins. These substances also find diversified uses, including foods, pharmaceuticals, detergents, products for daily use such as cosmetics, and a variety of chemical raw materials.

In industrial production of useful substances by use of microorganisms, improvement of productivity is one major topic of interest, and one approach therefor is breeding of microorganisms through mutagenesis or other genetic means. Recently, in particular, with advancement of microbial genetics and biotechnology, more efficient production of useful substances through gene recombination techniques attracts attention.

Studies on promoters necessary for gene transcription have heretofore been actively conducted. For example, in relation to *Bacillus subtilis*, as a promoter region which is useful in achieving powerful transcription of a gene encoding a heterologous protein or polypeptide, there have been utilized a promoter region of an alkaline cellulase gene originating from *Bacillus* sp. KSM-64 (FERM BP-2886) (see, for example, Non-Patent Document 1) and a promoter region which is found in an upstream site of an alkaline cellulase gene originating from *Bacillus* sp. KSM-S237 (FERM BP-7875).

However, in production on an industrial scale, reduction in production cost is necessary, and higher productivity is demanded, because the above-mentioned promoter regions currently in use do not necessarily promise sufficiently enhanced productivity.

Patent Document 1: JP-A-2000-210081
Non-Patent Document 1: Biosci. Biotech. Biochem., 59, 2172, (1995)

DISCLOSURE OF THE INVENTION

The present invention provides a promoter DNA which has been modified so that a nucleotide sequence containing a promoter recognized by SigA and bases in the vicinity thereof is recognized by SigA and SigE.

The present invention also provides an expression vector containing the promoter DNA, a recombinant organism containing the expression vector, and a method of producing a protein or polypeptide characterized by culturing the recombinant microorganism.

The present invention further provides a method of constructing a promoter DNA, characterized by modifying a nucleotide sequence containing a promoter recognized by SigA and bases in the vicinity thereof so that the promoter DNA is recognized by SigA and SigE.

MODE FOR CARRYING OUT THE INVENTION

Figure 1:
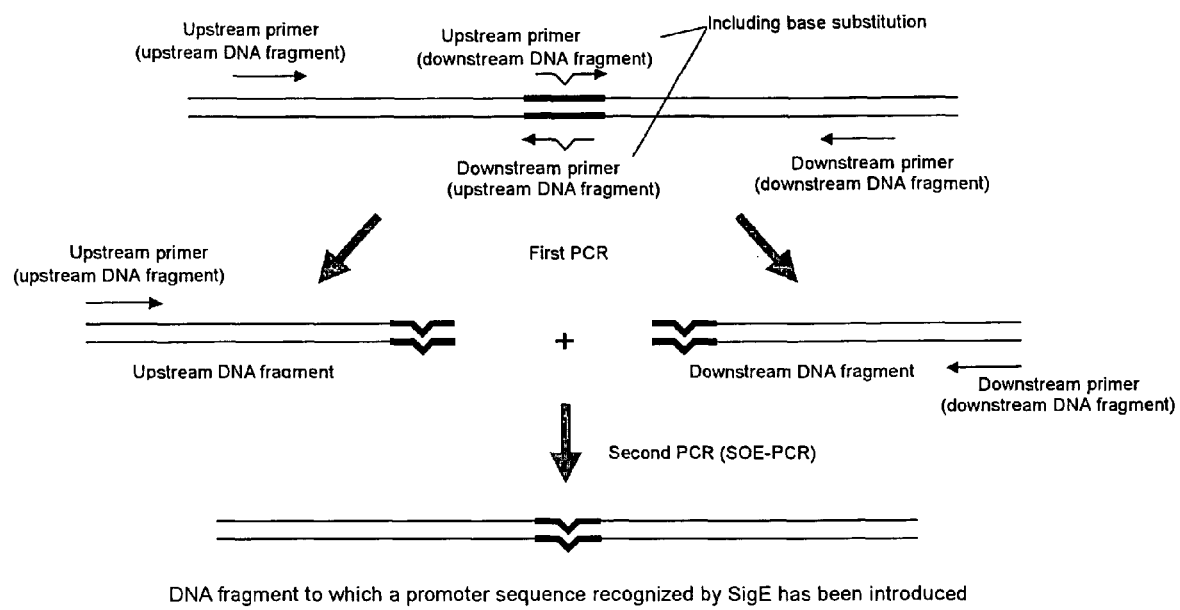
FIG. 1 A schematic chart showing a procedure for introducing a SigE-recognized promoter sequence by means of SOE-PCR.

The present invention provides a modified promoter DNA capable of increasing the transcriptional amount of a gene encoding a protein or polypeptide, as well as an efficient method for producing a protein or polypeptide through use of the modified promoter DNA.

In *Bacillus subtilis*, 17 sigma factors—which are subunits of an RNA polymerase complex—have been identified to be associated with recognition of a promoter sequence. They include SigA (also called a housekeeping sigma factor), which is a primary sigma factor that participates in transcription of a gene which is essential for growth during the vegetative growth period; SigH, SigF, SigE, SigG, and SigK, which control sporulation; SigD, which controls flagellum biogenesis and cell wall lysis; SigL, which controls metabolism of certain amino acids or saccharides; SigB, which controls the ability of adjustment to environmental changes; and a sigma factor named ECF sigma. Respective sigma factors, when bound to an RNA polymerase core complex composed of five subunits ($\alpha$, $\beta$, $\beta'$, $\delta$, $\omega$) other than a sigma factor, participate in recognition of a promoter sequence in such a manner that a different sigma factor recognizes different promoter sequence, to thereby attain transcription of different genes. This mechanism is considered to regulate expression, as the situation requires, of approximately 4,100 genes present on the genome.

During vegetative growth, through association with an RNA polymerase core complex, SigA is reported to predominantly direct transcription of a gene having a SigA-recognizable promoter, or an operon, and thereafter, during sporulation, when a sigma factor that controls the sporulation process is activated, substitution takes place to replace the sigma factor that is associated with the RNA polymerase core complex, resulting in a relative decrease in the amount of SigA-associated RNA polymerase (J. Bacteriol., 179, 4969 (1999)). Thus, during and after the sporulation stage, the level of transcription from a SigA-recognized promoter is considered to decrease as compared with the level in the vegetative growth stage.

Under the above circumstances, the present inventors have found that, through subjecting a DNA fragment having a promoter recognized by SigA which is a sigma factor of *Bacillus subtilis* to base modification through genetic engineering so as to newly construct a sequence recognized by SigE, with the recognition by SigA being maintained, transcription of genes encoding proteins or polypeptides ligated downstream of the modified promoter recognized by SigA and SigE can be enhanced.

When the promoter DNA of the present invention is employed, transcription of genes encoding proteins or polypeptides ligated downstream of the promoter DNA can be enhanced considerably as compared with a natural promoter, whereby proteins or polypeptides can be produced efficiently.

In the present invention, homology between amino acid sequences and that between nucleic acid sequences are both determined by use of the Lipman-Pearson method (Science, 227, 1435 (1985)). Specifically, calculation is performed by use of a homology analysis program (Search Homology) developed by genetic information processing software Genetyx-Win, (Software Development Co., Ltd.), with ktup (the unit size to be compared, employed as a parameter) being set to 2.

It is generally accepted that a sigma factor is bound to a sequence of several bases that is present in the vicinity of a 10-base upstream site or 35-base upstream site from the transcription start point. The sequences corresponding to these sites are called the −10 region and the −35 region, respectively. Moreover, it has been known that, for each sigma factor, common characteristics are shared by the base sequence and the distance between the two regions. Thus, such a sequence is called a consensus sequence, and is considered to form the essential part of the promoter. The consensus sequence of SigA is known to have a −35 region of TTGaca and a −10 region of tgnTAtaat, which is linked to a site 14 nucleotides downstream from the −35 region (n represents A, G, C, or T, and when nucleotides are shown with upper case letters, the nucleotides are highly conserved, whereas when nucleotides are shown with lower case letters, the nucleotides are not well conserved. See *Bacillus Subtilis and Its Closest Relatives: From Genes to Cells*, Edited by A. L. Sonenshein, American Society for Microbiology, pp 289, (2002)). Separately, several consensus sequences recognized by SigA are known to be present in a nucleotide sequence ranging from base Nos. 92 to 552 in SEQ ID NO: 1 and a nucleotide sequence ranging from base Nos. 133 to 589 in SEQ ID NO: 2 (Biosci Biotechnol Biochem. 64, 2281, 2000, Biosci Biotechnol Biochem. 56, 872, (1992)).

Therefore, preferred examples of the present nucleotide sequences having a promoter recognized by SigA and nucleotides in the vicinity of the promoter include the following: a nucleotide sequence ranging from base Nos. 92 to 552 in SEQ ID NO: 1; a nucleotide sequence ranging from base Nos. 133 to 589 in SEQ ID NO: 2; or a nucleotide sequence having a homology of 80% or more, preferably 90% or more, more preferably 95% or more, even more preferably 98% or more, to either of these sequences, and having a consensus sequence of SigA and/or promoter functions equivalent to those of the consensus sequence. Preferably, the present nucleotide sequences include a nucleotide sequence having a nucleotide sequence represented by SEQ ID NO: 1; a nucleotide sequence represented by SEQ ID NO: 2; or a nucleotide sequence having a homology of 90% to either of these sequences, preferably 95% or more, more preferably 98% or more, and having the consensus sequence which is recognized by SigA and/or promoter functions equivalent to those of the consensus sequence. The nucleotide sequences having a nucleotide sequence ranging from base Nos. 92 to 552 in SEQ ID NO: 1 are, in a nucleotide sequence in SEQ ID NO: 1, preferably a 461 to 570 bp consecutive nucleotide sequence having a nucleotide sequence of base Nos. 92 to 552, more preferably a 461 to 520 bp consecutive nucleotide sequence, even more preferably a 461 to 480 bp consecutive nucleotide sequence. The nucleotide sequences having a nucleotide sequence ranging from base Nos. 133 to 589 in SEQ ID NO: 2 are, in a nucleotide sequence represented by SEQ ID NO: 2, preferably a 457 to 610 bp consecutive nucleotide sequence having a nucleotide sequence of base Nos. 133 to 589, more preferably a 457 to 520 bp consecutive nucleotide sequence, even more preferably a 457 to 480 bp consecutive nucleotide sequence.

Here, a nucleotide sequence represented by SEQ ID NO: 1 is present upstream of an alkaline cellulase gene derived from *Bacillus* sp. KSM-S237 (FERM BP-7875), whereas a nucleotide sequence represented by SEQ ID NO: 2 is present upstream of an alkaline cellulase gene derived from *Bacillus* sp. KSM-64 (FERM BP-2886), the two nucleotide sequences having a homology of 95.6%.

The promoter DNA of the present invention may be constructed by subjecting the above nucleotide sequences to base modification so as to be recognized not only by SigE but also by SigA. The number of promoters to be constructed may be one, or alternatively two or more.

Promoter sequences recognized by SigE are reported to have a nucleotide sequence formed of a −35 region represented by ATAHTT (H denotes A, C, or T) and −10 region represented by CATAYAHT (Y denotes C or T), which is linked to the site 13 or 14 nucleotides downstream from the −35 region, preferably, a nucleotide sequence formed of a −35 region represented by ATATTT and a −10 region represented by CATACAAT, which is linked to the site 13 or 14 nucleotides downstream from the −35 region, and more preferably a nucleotide sequence represented by ATATTTCAAGTAG-TAATAACATACAAT (J. Mol. Biol. 327, 945, (2003)). Preferably, such nucleotide sequences are newly constructed.

Preferred promoter DNA in the present invention include a nucleotide sequence represented by SEQ ID NO: 7, which have been produced by modifying a nucleotide sequence represented by SEQ ID NO: 1, and a nucleotide sequence represented by SEQ ID NO: 8, which have been produced by modifying a nucleotide sequence represented by SEQ ID NO: 2.

Base modification is performed through insertion of a DNA fragment having a promoter sequence recognized by SigE, or through deletion, substitution, or insertion of one or more bases. Of these modifications, substitution of one or more bases is preferred. Specifically, a promoter DNA having an inserted promoter sequence recognized by SigE can be constructed as follows. A restriction enzyme recognition site is introduced into any site of a DNA fragment (SEQ ID NO: 1) originating from a region upstream of an alkaline cellulase gene from *Bacillus* sp. KSM-S237 (FERM BP-7875), which gene had been introduced into a plasmid vector by cloning, or of a DNA fragment (SEQ ID NO: 2) derived from a region upstream of an alkaline cellulase gene derived from *Bacillus* sp. KSM-64 (FERM BP-2886) etc., which gene had been introduced into a plasmid vector by cloning, through site-specific mutagenesis such as the Kunkel method (Proc. Natl. Acad. Sci. USA., 82, 488, 1985). Separately, a DNA fragment having the promoter sequence recognized by SigE is prepared through chemical synthesis or a similar method so as to have a restriction enzyme recognition site at each end; and the thus-prepared two fragments, which have been treated with the same restriction enzyme, are ligated with ligase.

Alternatively, the above DNA can be constructed through subjecting a potion of a DNA fragment derived from an upstream region of an alkaline cellulase gene represented by SEQ ID NO: 1 or SEQ ID NO: 2 to base substitution through the SOE (splicing by overlap extension)-PCR method (Gene, 77, 51, 1989) or a similar method.

Next will be described in more detail a method for newly constructing a promoter (sequence) recognized by SigE through subjecting a potion of a DNA fragment having a nucleotide sequence of SEQ ID NO: 1 to base substitution through the SOE-PCR method.

In the first PCR, the following two fragments are prepared: an upstream DNA fragment containing a site having a substituted base at the downstream end, and a downstream DNA fragment containing a site having a substituted base at the upstream end. In this step, above-described DNA fragments are designed so as to anneal with two primers, each of which is respectively designed for downstream of the upstream DNA fragment and upstream of the downstream DNA fragment, for example, and at the same time, the above-described DNA fragments are constructed in a way as to contain the promoter sequence recognized by SigE (FIG. 1).

Next, using the two DNA fragments prepared in the first PCR as templates, the second PCR is performed by use of an upstream primer of the upstream DNA fragment and a downstream primer of the downstream DNA fragment. As a result, the downstream end of the upstream DNA fragment anneals with the upstream end of the downstream DNA fragment through the overlapping sequences. The two DNA fragments are ligated through PCR amplification, to thereby obtain a DNA fragment having newly constructed promoter sequence recognized by SigE at a ligation site (FIG. 1).

The thus-constructed promoter DNA is recognized not only by SigE but also by SigA, facilitating transcription, during the sporulation stage, of a gene encoding a protein or polypeptide ligated downstream of the above promoter DNA.

Specifically, when a heterologous protein or polypeptide is produced by use of *Bacillus subtilis* through a recombinant technique, through ligation of the promoter DNA to a site upstream of a gene encoding the target protein or polypeptide, during the vegetative stage, the genes can be transcribed by RNA polymerase bound to SigA, and during the sporulation stage which follows the vegetative stage, the gene can be transcribed by RNA polymerase bound to SigE, thus achieving continued transcription during the sporulation stage. Therefore, when a recombinant *Bacillus subtilis* introduced by a expression vector containing the above promoter DNA is employed, the target proteins or polypeptides can be produced considerably, as compared with *Bacillus subtilis* having a natural promoter other than the newly constructed promoter recognized by SigE.

No particular limitation is imposed on the gene encoding the target protein or polypeptide. Examples of the protein and polypeptide include physiologically-active peptides and enzymes for industrial purposes such as detergents, foods, fibers, feeds, chemicals, medicine, and diagnostic agents. Industrial enzymes may be functionally grouped into oxidoreductases, transferases, hydrolases, lyases, isomerases, and ligases/synthetases. Preferably, hydrolases such as cellulase, α-amylase, and protease may be used. Specific examples include cellulase belonging to family 5 in the classification of enzymes which hydrolyze polysaccharides (Biochem. J., 280, 309, (1991)); in particular, cellulase derived from a microorganism, more particularly cellulase derived from the genus *Bacillus*. More specific examples include alkaline cellulase having an amino acid sequence of SEQ ID NO: 4 which is derived from *Bacillus* sp. KSM-S237 (FERM BP-7875), alkaline cellulase having an amino acid sequence of SEQ ID NO: 6 which is derived from *Bacillus* sp. KSM-64 (FERM BP-2886), and cellulase which has another amino acid sequence having a homology of 70% or more to said amino acid sequence, preferably 80% or more, more preferably 90% or more, further preferably 95% or more, or still further preferably 98% or more.

Specific examples of α-amylase include α-amylase derived from a microorganism, preferably liquefied amylase derived from the genus *Bacillus*. More specific examples include alkaline amylase having an amino acid sequence of SEQ ID NO: 14 which is derived from *Bacillus* sp. KSM-K38 (FERM BP-6946), and amylase which has another amino-acid sequence having a homology of 70% or more to said amino-acid sequence, preferably 80% or more, more preferably 90% or more, further preferably 95% or more, even more preferably 98% or more. Specific examples of protease include serine protease and metalloprotease which are derived from microorganisms, particularly those belonging to the genus *Bacillus*.

In addition to the promoter DNA of the present invention, preferably, regulatory regions related to secretion or translation of the target protein or polypeptide; i.e., a ribosome-bound site (SD sequence), a translation initiation region including the initiation codon, and a secretion signal peptide region, are properly ligated to the gene of the target protein or polypeptide. In one preferred example, a transcription initiation regulatory region, a translation initiation region, and a secretion signal peptide region of a cellulase gene derived from a microorganism belonging to the genus *Bacillus* disclosed in, for example, JP-A-2000-210081 or JP-A-1992-190793; i.e., a cellulase gene derived from KSM-S237 (FERM BP-7875) or KSM-64 (FERM BP-2886), is properly ligated to a structural gene of the target protein or polypeptide. More specifically, preferred DNA fragments to be ligated include a nucleotide sequence ranging from base Nos. 563 to 659 of SEQ ID NO: 3; a nucleotide sequence ranging from base Nos. 600 to 696 of a cellulase gene of SEQ ID NO: 5; a DNA fragment having a nucleotide sequence having a homology of 70% or more to any one of said nucleotide sequences, preferably 80% or more, more preferably 90% or more, further preferably 95% or more, further more preferably 98% or more; or a DNA fragment having a nucleotide sequence lacking a portion of any one of said nucleotide sequences. Preferably, one of these DNA fragments is properly ligated to a structural gene of the target protein or polypeptide.

Productivity of the target protein or polypeptide can be enhanced by use of a recombinant microorganism, which is constructed by transferring an expression vector into a *Bacillus subtilis* cell through a conventional transformation technique. The expression vector is produced by ligating the promoter DNA of the present invention upstream of a DNA fragment containing the above gene encoding the target protein or polypeptide, and inserting the thus-ligated DNA fragment into an appropriate vector. Alternatively, the promoter DNA of the present invention is ligated to an appropriate region which is homologous with the genome of *Bacillus subtilis*, to thereby prepare a DNA fragment. The DNA fragment is inserted directly into the genome of *Bacillus subtilis*, to thereby construct a recombinant cell strain. Productivity of the target protein or polypeptide may be enhanced by use of the recombinant cell strain.

The target protein or polypeptide obtained by use of the promoter DNA of the present invention may be produced in such a manner that the above recombinant microorganism is inoculated onto a culture medium containing assimilable carbon sources and nitrogen sources, and other essential components; the microorganism is cultured through a conventional microorganism culturing method; and subsequently, protein or polypeptide is collected and purified.

Next, a method for constructing a DNA fragment of the present invention and a method for producing cellulase through a recombinant technique with the DNA fragment will be described in detail by way of Examples.

EXAMPLES

Example 1

Figure 2:
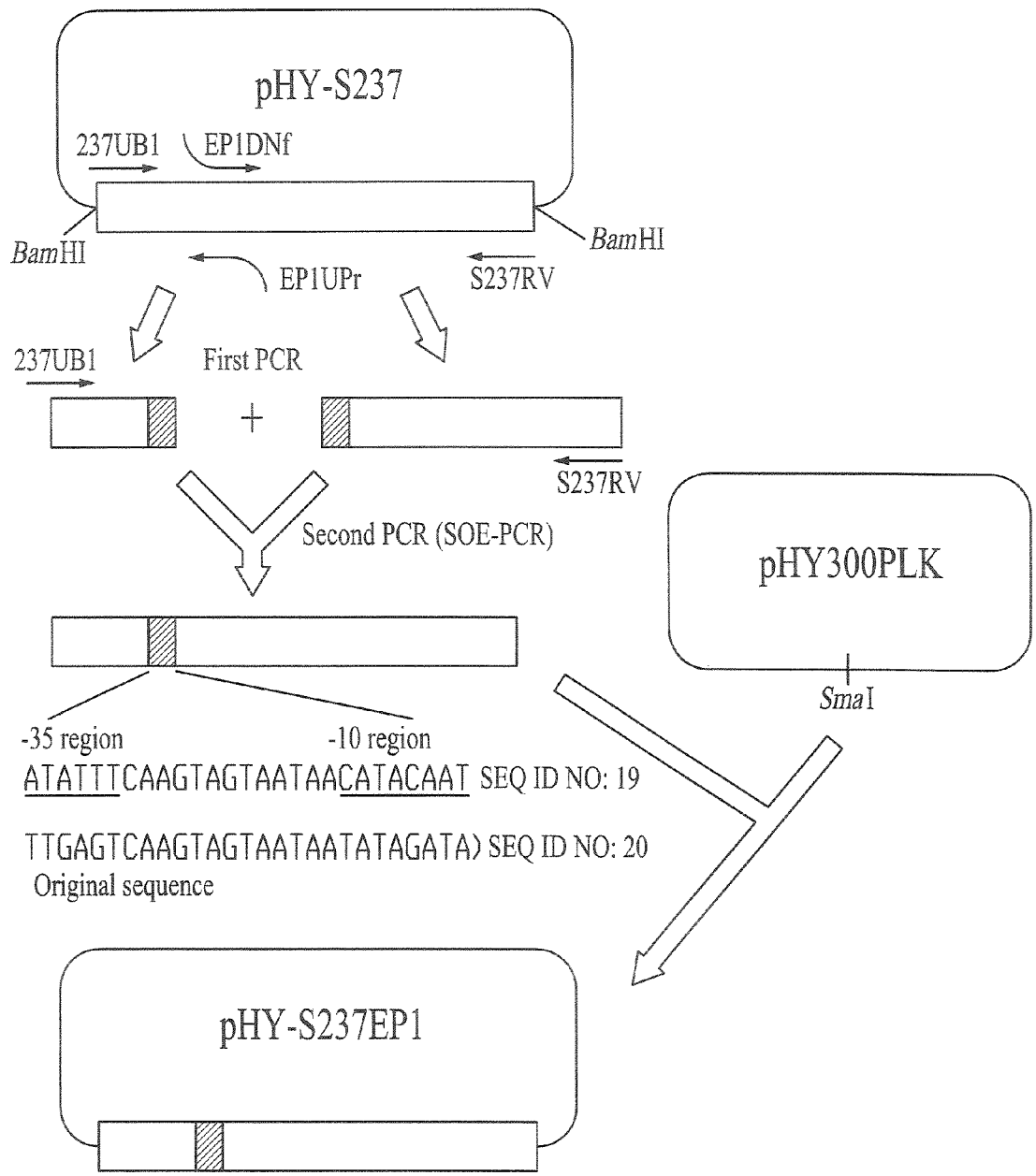
FIG. 2 A schematic chart showing a method of constructing a plasmid for producing alkaline cellulase, wherein the plasmid has been modified so as to contain a SigE-recognized promoter sequence.

Construction of Promoter (Sequence) Recognized by SigE in Upstream Region of Alkaline Cellulase Gene A promoter recognized by SigE was introduced into an upstream region of an alkaline cellulase gene in accordance with the procedure as shown in FIG. 2. Specifically, a recombinant plasmid pHY-S237, serving as a template, and a primer set of 237UB1 and EP1UPr shown in Table 1 were employed, to thereby prepare an upstream region of an alkaline cellulase gene; i.e., a 0.4 kb fragment (A). The recombinant plasmid pHY-S237 was prepared by inserting a DNA fragment (3.1 kb) encoding an alkaline cellulase gene (JP-A-2000-210081) derived from *Bacillus* sp. KSM-S237 (FERM BP-7875) into the restriction enzyme BamHI cleavage site of a shuttle vector pHY300PLK. Similarly, a primer set of EP1DNf and S237RV shown in Table 1 was employed, to thereby prepare a downstream region of an alkaline cellulase gene; i.e., a 2.7 kb fragment (B). Subsequently, SOE-PCR was performed by use of a primer set of 237UB1 and S237RV shown in Table 1 and the two fragments (A) and (B) as a template mixture, to thereby produce a 3.1 kb DNA fragment (C) in which the fragments (A) and (B) were ligated in this sequence. Primers EP1UPr and EP1DNf had been subjected to base substitution treatment, and, as shown in FIG. 2, the DNA fragment (C) contained a newly constructed promoter (sequence) recognized by SigE in a region about 150 bp upstream from the translation initiation site of the alkaline cellulase. The thus-obtained 3.1 kb DNA fragment (C) was inserted into the SmaI restriction enzyme cleavage site of a shuttle vector pHY300PLK, to thereby construct a recombinant plasmid pHY-S237EP1. Separately, the recombinant plasmid pHY-S237, serving as a template, and a primer set of 237UB1 and S237RV shown in Table 1 were employed, to thereby prepare a 3.1 kb fragment (D) containing a full length alkaline cellulase gene. Subsequently, the 3.1 kb fragment (D) was inserted into the SmaI restriction enzyme cleavage site of a shuttle vector pHY300PLK, to thereby construct a recombinant plasmid pHY-S237W.

Example 2

Evaluation of Alkaline Cellulase Production (Secretion) Performance

The recombinant plasmid pHY-S237EP1 obtained in Example 1 and a recombinant plasmid pHY-S237W serving as a control were individually introduced to cells of *Bacillus subtilis* 168 through the protoplast transformation method. The cells were shake-cultured in LB medium (10 mL) overnight at 37° C. The culture broth (0.05 mL) was inoculated to a 2×L-maltose medium (50 mL) (2% tryptone, 1% yeast extract, 1% NaCl, 7.5% maltose, 7.5 ppm manganese sulfate 4-5 hydrate, and 15 ppm tetracycline), followed by shake-culturing at 30° C. for three days. After completion of culturing, cells were removed through centrifugation, and alkaline cellulase activity of the supernatant obtained from the culture was determined for calculation of the amount of the alkaline cellulase secreted from the cells during culturing; i.e., the amount of the extracellularly produced alkaline cellulase. As is clear from Table 2, more effective production, or secretion, of alkaline cellulase has been confirmed in the case where pHY-S237EP1 was employed as a recombinant plasmid, as compared with the control pHY-S237W (wild type). Thus, use of pHY-S237EP1 enhances cellulase production or secretion, conceivably because transcription from the newly constructed promoter recognized by SigE was added to transcription from a promoter recognized by SigA.

TABLE 1

| Primer | Nucleotide sequence | SEQ ID NO. |
|---|---|---|
| 237UB1 | TTGCGGATCCAACAGGCTTATATTTAGAGGAAATTTC | 9 |
| EP1UPr | GTATGTTATTACTACTTGAAATATTCTACCCCCCTTCCTA | 10 |
| EP1DNf | ATATTTCAAGTAGTAATAACATACAATACTTATAAGTTG | 11 |
| S237RV | TCGCTACCCTTTTATTATCG | 12 |

TABLE 2

| Recombinant plasmid | Amount of produced (secreted) alkaline cellulase (relative value) |
|---|---|
| pHY-S237W (wild type) | 100 |
| pHY-S237EP1 | 165 |

Example 3

Alkaline Amylase Production Performance of Upstream Region of Alkaline Cellulase Gene Containing Promoter (Sequence) Recognized by SigE The plasmid pHY-S237EP1 constructed in Example 1, serving as a template, and a primer set of S237ppp-F2 (BamHI) and S237ppp-R2 (ALAA) shown in Table 3 were employed, to thereby amplify through PCR a 0.6 kb DNA fragment (E) containing a region encoding a secretory signal sequence and a promoter region of the alkaline cellulase to which an SigE-recognized promoter (sequence) has been transferred. Separately, PCR was performed using a genome DNA sample extracted from *Bacillus* sp. KSM-K38 (FERM BP-6946) as a template, and a primer set of K38matu-F2 (ALAA) and SP64K38-R (XbaI) shown in Table 3, whereby a 1.5 kb DNA fragment (F) encoding alkaline amylase (Appl. Environ. Microbiol., 67, 1744, (2001)) having an amino acid sequence of SEQ ID NO: 14 was amplified. Subsequently, SOE-PCR was performed by use of a primer set of S237ppp-F2 (BamHI) and SP64K38-R (XbaI) shown in Table 3 and the thus-obtained two fragments (E) and (F) (in a mixture form) as templates, to thereby produce a 2.1 kb DNA fragment (G) in which an alkaline amylase gene was ligated downstream of the region encoding a secretory signal sequence followed by the promoter region, containing a promoter (sequence) recognized by SigE, of an alkaline cellulase gene. The thus-produced 2.2 kb DNA fragment (G) was inserted into the BamHI-XbaI restriction enzyme cleavage site of a shuttle vector pHY300PLK (yakult), to thereby construct a recombinant plasmid pHY-K38 (S237ps) EP1. Separately, the above procedure was repeated, except that the plasmid pHY-S237W constructed in Example 1 was employed instead of the template which had been employed for amplification of the aforementioned 0.6 kb DNA fragment (E), to thereby construct a recombinant plasmid pHY-K38 (S237ps) W.

The thus-constructed plasmid pHY-K38 (S237ps) EP1 and pHY-K38 (S237ps) W (which serves as a control) were individually introduced to cells of *Bacillus subtilis* 168 through the protoplast transformation method. The cells were shake-cultured for five days, and other conditions were the same as employed in Example 2. After completion of culturing, cells were removed through centrifugation, and alkaline amylase activity of the supernatant obtained from the culture was determined for calculation of the amount of the amylase secreted from the cells during culturing; i.e., the amount of the extracellularly produced amylase. As is clear from Table 4, more effective production, or secretion, of alkaline amylase has been confirmed in the case where pHY-K38 (S237ps) EP1 was employed as a recombinant plasmid, as compared with the control pHY-K38 (S237ps) W (wild type). Thus, it was revealed that the upstream region, containing a promoter (sequence) recognized by SigE, of an alkaline cellulase gene were employed effectively in producing a variety of proteins or polypeptides.

TABLE 3

| Primer | Nucleotide sequence | SEQ ID NO. |
|---|---|---|
| S237ppp-F2 (BamHI) | CCCGGATCCAACAGGCTTATATTTA | 15 |
| S237ppp-R2 (ALAA) | TTCAATCCATCTGCTGCAAGAGCTGCCGG | 16 |
| K38matu-F2 (ALAA) | GCTCTTGCAGCAGATGGATTGAACGGTACG | 17 |
| SP64K38-R (XbaI) | TTGGTCTAGACCCCAAGCTTCAAAGTCGTA | 18 |

TABLE 4

| Recombinant plasmid | Amount of produced (secreted) alkaline amylase (relative value) |
|---|---|
| pHY-K38 (S237ps) W (wild type) | 100 |
| pHY-K38 (S237ps) EP1 | 143 |

SEQUENCE LISTING

<160> NUMBER OF SEQ ID NOS: 20

<210> SEQ ID NO 1
<211> LENGTH: 572
<212> TYPE: DNA
<213> ORGANISM: Bacillus sp. KSM-S237

<400> SEQUENCE: 1

```
gatttgccga tgcaacaggc ttatatttag aggaaatttc ttttaaatt gaatacggaa        60 taaaatcagg taaacaggtc ctgatttat ttttttgagt ttttagaga actgaagatt       120 gaaataaaag tagaagacaa aggacataag aaaattgcat tagttttaat tatagaaaac       180 gccttttat aattatttat acctagaacg aaaatactgt ttcgaaagcg gtttactata       240
aaaccttata ttccggctct tttttaaaac aggggtaaa aattcactct agtattctaa       300
tttcaacatg ctataataaa tttgtaagac gcaatatgca tctcttttt tacgatatat       360 gtaagcggtt aaccttgtgc tatatgccga tttaggaagg ggggtagatt gagtcaagta       420
gtaataatat agataactta taagttgttg agaagcagga gagcatctgg gttactcaca       480 agtttttta aaactttaac gaaagcactt tcggtaatgc ttatgaattt agctatttga       540
ttcaattact ttaaaaatat ttaggaggta at                                    572
```

<210> SEQ ID NO 2
<211> LENGTH: 609
<212> TYPE: DNA
<213> ORGANISM: Bacillus sp. KSM-64

<400> SEQUENCE: 2

```
agtacttacc attttagagt caaagatag aagccaagca ggatttgccg atgcaaccgg        60
cttatattta gagggaattt cttttaaat tgaatacgga ataaaatcag gtaaacaggt       120
cctgatttta ttttttgaa ttttttgag aactaaagat tgaaatagaa gtagaagaca       180
acggacataa gaaaattgta ttagttttaa ttatagaaaa cgcttttcta taattattta       240
tacctagaac gaaaatactg tttcgaaagc ggtttactat aaaaccttat attccggctc       300
tttttttaaa caggggtga aaattcactc tagtattcta atttcaacat gctataataa       360
```

| | | |
|---|---|---|
| atttgtaaga cgcaatatac atcttttttt tatgatattt gtaagcggtt aaccttgtgc | 420 | |
| tatatgccga tttaggaagg gggtagattg agtcaagtag tcataattta gataacttat | 480 | |
| aagttgttga gaagcaggag agaatctggg ttactcacaa gttttttaaa acattatcga | 540 | |
| aagcactttc ggttatgctt atgaatttag ctatttgatt caattacttt ataattttta | 600 | |
| ggaggtaat | 609 | |

<210> SEQ ID NO 3
<211> LENGTH: 3149
<212> TYPE: DNA
<213> ORGANISM: Bacillus sp. KSM-S237

<400> SEQUENCE: 3

| | | |
|---|---|---|
| gatttgccga tgcaacaggc ttatatttag aggaaatttc tttttaaatt gaatacggaa | 60 | |
| taaaatcagg taaacaggtc ctgatttat tttttgagt ttttagaga actgaagatt | 120 | |
| gaaataaaag tagaagacaa aggacataag aaaattgcat tagttttaat tatagaaaac | 180 | |
| gccttttat aattatttat acctagaacg aaaatactgt ttcgaaagcg gtttactata | 240 | |
| aaaccttata ttccggctct tttttaaaac aggggggtaaa aattcactct agtattctaa | 300 | |
| tttcaacatg ctataataaa tttgtaagac gcaatatgca tctcttttt tacgatatat | 360 | |
| gtaagcggtt aaccttgtgc tatatgccga tttaggaagg gggtagatt gagtcaagta | 420 | |
| gtaataatat agataactta aagttgttg agaagcagga gagcatctgg gttactcaca | 480 | |
| agttttttta aaactttaac gaaagcactt tcggtaatgc ttatgaattt agctatttga | 540 | |
| ttcaattact ttaaaaatat ttaggaggta atatgtgtta agaaagaaaa caaagcagtt | 600 | |
| gatttcttcc attcttattt tagttttact tctatctta tttccggcag ctcttgcagc | 660 | |
| agaaggaaac actcgtgaag acaatttaa acatttatta ggtaatgaca atgttaaacg | 720 | |
| cccttctgag gctggcgcat acaattaca agaagtcgat ggacaaatga cattagtaga | 780 | |
| tcaacatgga gaaaaaattc aattacgtgg aatgagtaca cacggattac agtggtttcc | 840 | |
| tgagatcttg aatgataacg catacaaagc tctttctaac gattgggatt ccaatatgat | 900 | |
| tcgtcttgct atgtatgtag gtgaaaatgg gtacgctaca aaccctgagt taatcaaaca | 960 | |
| aagagtgatt gatggaattg agttagcgat tgaaaatgac atgtatgtta ttgttgactg | 1020 | |
| gcatgttcat gcgccaggtg atcctagaga tcctgtttat gcaggtgcta agatttcttt | 1080 | |
| tagagaaatt gcagctttat accctaataa tccacacatt atttatgagt tagcgaatga | 1140 | |
| gccgagtagt aataataatg gtggagcagg gattccgaat aacgaagaag gttggaaagc | 1200 | |
| ggtaaaagaa tatgctgatc caattgtaga aatgttacgt aaaagcggta atgcagatga | 1260 | |
| caacattatc attgttggta gtccaaactg gagtcagcgt ccggacttag cagctgataa | 1320 | |
| tccaattgat gatcaccata caatgtatac tgttcacttc tacactggtt cacatgctgc | 1380 | |
| ttcaactgaa agctatccgt ctgaaactcc taactctgaa agaggaaacg taatgagtaa | 1440 | |
| cactcgttat gcgttagaaa acggagtagc ggtatttgca acagagtggg gaacgagtca | 1500 | |
| agctagtgga gacggtggtc cttactttga tgaagcagat gtatggattg aatttttaaa | 1560 | |
| tgaaaacaac attagctggg ctaactggtc tttaacgaat aaaaatgaag tatctggtgc | 1620 | |
| atttacacca ttcgagttag gtaagtctaa cgcaaccaat cttgacccag gtccagatca | 1680 | |
| tgtgtgggca ccagaagaat taagtctttc tggagaatat gtacgtgctc gtattaaagg | 1740 | |
| tgtgaactat gagccaatcg accgtacaaa atacacgaaa gtactttggg actttaatga | 1800 | |
| tggaacgaag caaggatttg gagtgaattc ggattctcca aataaagaac ttattgcagt | 1860 | |

-continued

```
tgataatgaa acaacacttt tgaaagtttc gggattagat gtaagtaacg atgtttcaga    1920
tggcaacttc tgggctaatg ctcgtctttc tgccaacggt tggggaaaaa gtgttgatat    1980
tttaggtgct gagaagctta caatggatgt tattgttgat gaaccaacga cggtagctat    2040
tgcggcgatt ccacaaagta gtaaagtgg atgggcaaat ccagagcgtg ctgttcgagt    2100
gaacgcggaa gattttgtcc agcaaacgga cggtaagtat aaagctggat taacaattac    2160
aggagaagat gctcctaacc taaaaaatat cgcttttcat gaagaagata caatatgaa     2220 caacatcatt ctgttcgtgg aactgatgc agctgacgtt atttacttag ataacattaa     2280
agtaattgga acagaagttg aaattccagt tgttcatgat ccaaaaggag aagctgttct    2340
tccttctgtt tttgaagacg gtacacgtca aggttgggac tgggctggag agtctggtgt    2400
gaaaacagct ttaacaattg aagaagcaaa cggttctaac gcgttatcat gggaatttgg    2460
atatccagaa gtaaaaccta gtgataactg gcaacagct ccacgtttag atttctggaa     2520
atctgacttg gttcgcggtg agaatgatta tgtagctttt gatttctatc tagatccagt    2580
tcgtgcaaca gaaggcgcaa tgaatatcaa tttagtattc cagccaccta ctaacgggta    2640
ttgggtacaa gcaccaaaaa cgtatacgat taactttgat gaattagagg aagcgaatca    2700
agtaaatggt ttatatcact atgaagtgaa aattaacgta agagatatta caaacattca    2760
agatgacacg ttactacgta acatgatgat catttttgca gatgtagaaa gtgactttgc    2820
agggagagtc tttgtagata atgttcgttt tgaggggct gctactactg agccggttga     2880
accagagcca gttgatcctg gcgaagagac gccacctgtc gatgagaagg aagcgaaaaa    2940
agaacaaaaa gaagcagaga agaagagaa agaagcagta aagaagaaa agaaagaagc      3000 taaagaagaa aagaaagcag tcaaaaatga ggctaagaaa aataatctaa ttaaactagt    3060
tatagggtta tctaaaggtc tgatgtagat cttttagata acctttttct tgcataactg    3120
gacacagagt tgttattaaa gaaagtaag                                      3149
```

<210> SEQ ID NO 4
<211> LENGTH: 795
<212> TYPE: PRT
<213> ORGANISM: Bacillus sp. KSM-S237

<400> SEQUENCE: 4

```
Ala Glu Gly Asn Thr Arg Glu Asp Asn Phe Lys His Leu Leu Gly Asn
1               5                   10                  15

Asp Asn Val Lys Arg Pro Ser Glu Ala Gly Ala Leu Gln Leu Gln Glu
                20                  25                  30

Val Asp Gly Gln Met Thr Leu Val Asp Gln His Gly Glu Lys Ile Gln
            35                  40                  45

Leu Arg Gly Met Ser Thr His Gly Leu Gln Trp Phe Pro Glu Ile Leu
        50                  55                  60

Asn Asp Asn Ala Tyr Lys Ala Leu Ser Asn Asp Trp Asp Ser Asn Met
65                  70                  75                  80

Ile Arg Leu Ala Met Tyr Val Gly Glu Asn Gly Tyr Ala Thr Asn Pro
                85                  90                  95

Glu Leu Ile Lys Gln Arg Val Ile Asp Gly Ile Glu Leu Ala Ile Glu
            100                 105                 110

Asn Asp Met Tyr Val Ile Val Asp Trp His Val His Ala Pro Gly Asp
        115                 120                 125

Pro Arg Asp Pro Val Tyr Ala Gly Ala Lys Asp Phe Phe Arg Glu Ile
    130                 135                 140
```

```
Ala Ala Leu Tyr Pro Asn Asn Pro His Ile Ile Tyr Glu Leu Ala Asn
145                 150                 155                 160

Glu Pro Ser Ser Asn Asn Gly Gly Ala Gly Ile Pro Asn Asn Glu
            165                 170                 175

Glu Gly Trp Lys Ala Val Lys Glu Tyr Ala Asp Pro Ile Val Glu Met
            180                 185                 190

Leu Arg Lys Ser Gly Asn Ala Asp Asp Asn Ile Ile Ile Val Gly Ser
            195                 200                 205

Pro Asn Trp Ser Gln Arg Pro Asp Leu Ala Ala Asp Asn Pro Ile Asp
210                 215                 220

Asp His His Thr Met Tyr Thr Val His Phe Tyr Thr Gly Ser His Ala
225                 230                 235                 240

Ala Ser Thr Glu Ser Tyr Pro Ser Glu Thr Pro Asn Ser Glu Arg Gly
            245                 250                 255

Asn Val Met Ser Asn Thr Arg Tyr Ala Leu Glu Asn Gly Val Ala Val
            260                 265                 270

Phe Ala Thr Glu Trp Gly Thr Ser Gln Ala Ser Gly Asp Gly Gly Pro
            275                 280                 285

Tyr Phe Asp Glu Ala Asp Val Trp Ile Glu Phe Leu Asn Glu Asn Asn
290                 295                 300

Ile Ser Trp Ala Asn Trp Ser Leu Thr Asn Lys Asn Glu Val Ser Gly
305                 310                 315                 320

Ala Phe Thr Pro Phe Glu Leu Gly Lys Ser Asn Ala Thr Asn Leu Asp
            325                 330                 335

Pro Gly Pro Asp His Val Trp Ala Pro Glu Leu Ser Leu Ser Gly
            340                 345                 350

Glu Tyr Val Arg Ala Arg Ile Lys Gly Val Asn Tyr Glu Pro Ile Asp
            355                 360                 365

Arg Thr Lys Tyr Thr Lys Val Leu Trp Asp Phe Asn Asp Gly Thr Lys
370                 375                 380

Gln Gly Phe Gly Val Asn Ser Asp Ser Pro Asn Lys Glu Leu Ile Ala
385                 390                 395                 400

Val Asp Asn Glu Asn Asn Thr Leu Lys Val Ser Gly Leu Asp Val Ser
            405                 410                 415

Asn Asp Val Ser Asp Gly Asn Phe Trp Ala Asn Ala Arg Leu Ser Ala
            420                 425                 430

Asn Gly Trp Gly Lys Ser Val Asp Ile Leu Gly Ala Glu Lys Leu Thr
            435                 440                 445

Met Asp Val Ile Val Asp Glu Pro Thr Thr Val Ala Ile Ala Ala Ile
450                 455                 460

Pro Gln Ser Ser Lys Ser Gly Trp Ala Asn Pro Glu Arg Ala Val Arg
465                 470                 475                 480

Val Asn Ala Glu Asp Phe Val Gln Gln Thr Asp Gly Lys Tyr Lys Ala
            485                 490                 495

Gly Leu Thr Ile Thr Gly Glu Asp Ala Pro Asn Leu Lys Asn Ile Ala
            500                 505                 510

Phe His Glu Glu Asp Asn Asn Met Asn Asn Ile Ile Leu Phe Val Gly
            515                 520                 525

Thr Asp Ala Ala Asp Val Ile Tyr Leu Asp Asn Ile Lys Val Ile Gly
            530                 535                 540

Thr Glu Val Glu Ile Pro Val His Asp Pro Lys Gly Glu Ala Val
545                 550                 555                 560

Leu Pro Ser Val Phe Glu Asp Gly Thr Arg Gln Gly Trp Asp Trp Ala
            565                 570                 575
```

```
Gly Glu Ser Gly Val Lys Thr Ala Leu Thr Ile Glu Ala Asn Gly
            580                 585                 590

Ser Asn Ala Leu Ser Trp Glu Phe Gly Tyr Pro Glu Val Lys Pro Ser
        595                 600                 605

Asp Asn Trp Ala Thr Ala Pro Arg Leu Asp Phe Trp Lys Ser Asp Leu
    610                 615                 620

Val Arg Gly Glu Asn Asp Tyr Val Ala Phe Asp Phe Tyr Leu Asp Pro
625                 630                 635                 640

Val Arg Ala Thr Glu Gly Ala Met Asn Ile Asn Leu Val Phe Gln Pro
                645                 650                 655

Pro Thr Asn Gly Tyr Trp Val Gln Ala Pro Lys Thr Tyr Thr Ile Asn
            660                 665                 670

Phe Asp Glu Leu Glu Glu Ala Asn Gln Val Asn Gly Leu Tyr His Tyr
        675                 680                 685

Glu Val Lys Ile Asn Val Arg Asp Ile Thr Asn Ile Gln Asp Asp Thr
    690                 695                 700

Leu Leu Arg Asn Met Met Ile Ile Phe Ala Asp Val Glu Ser Asp Phe
705                 710                 715                 720

Ala Gly Arg Val Phe Val Asp Asn Val Arg Phe Glu Gly Ala Ala Thr
                725                 730                 735

Thr Glu Pro Val Glu Pro Glu Pro Val Asp Pro Gly Glu Glu Thr Pro
            740                 745                 750

Pro Val Asp Glu Lys Glu Ala Lys Lys Glu Gln Lys Glu Ala Glu Lys
        755                 760                 765

Glu Glu Lys Glu Ala Val Lys Glu Glu Lys Lys Glu Ala Lys Glu Glu
    770                 775                 780

Lys Lys Ala Val Lys Asn Glu Ala Lys Lys Lys
785                 790                 795

<210> SEQ ID NO 5
<211> LENGTH: 3332
<212> TYPE: DNA
<213> ORGANISM: Bacillus sp. KSM-64

<400> SEQUENCE: 5
agtacttacc attttagagt caaaagatag aagccaagca ggatttgccg atgcaaccgg      60
cttatattta gagggaattt cttttttaaat tgaatacgga ataaaatcag gtaaacaggt    120
cctgatttta ttttttgaa ttttttgag aactaaagat tgaaatagaa gtagaagaca      180
acggacataa gaaaattgta ttagtttaa ttatagaaaa cgcttttcta taattattta     240
tacctagaac gaaaatactg tttcgaaagc ggtttactat aaaaccttat attccggctc    300 ttttttaaa caggggtga aaattcactc tagtattcta atttcaacat gctataataa      360
atttgtaaga cgcaatatac atctttttt tatgatattt gtaagcggtt aaccttgtgc    420
tatatgccga tttaggaagg gggtagattg agtcaagtag tcataattta gataacttat   480
aagttgttga gaagcaggag agaatctggg ttactcacaa gtttttttaaa acattatcga   540 aagcactttc ggttatgctt atgaatttag ctatttgatt caattacttt aataattta    600 ggaggtaata tgatgttaag aaagaaaaca aagcagttga tttcttccat tcttatttta   660
gttttacttc tatctttatt tccgacagct cttgcagcag aaggaaacac tcgtgaagac    720
aattttaaac atttattagg taatgacaat gttaaacgcc cttctgaggc tggcgcatta    780
caattacaag aagtcgatgg acaaatgaca ttagtagatc aacatggaga aaaaattcaa    840
ttacgtggaa tgagtacaca cggattacaa tggtttcctg agatcttgaa tgataacgca    900
```

```
tacaaagctc ttgctaacga ttgggaatca aatatgattc gtctagctat gtatgtcggt    960
gaaaatggct atgcttcaaa tccagagtta attaaaagca gagtcattaa aggaatagat   1020
cttgctattg aaaatgacat gtatgtcatc gttgattggc atgtacatgc acctggtgat   1080
cctagagatc ccgtttacgc tggagcagaa gatttcttta gagatattgc agcattatat   1140
cctaacaatc cacacattat ttatgagtta gcgaatgagc caagtagtaa caataatggt   1200
ggagctggga ttccaaataa tgaagaaggt tggaatgcgg taaaagaata cgctgatcca   1260
attgtagaaa tgttacgtga tagcgggaac gcagatgaca atattatcat tgtgggtagt   1320
ccaaactgga gtcagcgtcc tgacttagca gctgataatc caattgatga tcaccataca   1380
atgtatactg ttcacttcta cactggttca catgctgctt caactgaaag ctatccgcct   1440
gaaactccta actctgaaag aggaaacgta atgagtaaca ctcgttatgc gttagaaaac   1500
ggagtagcag tatttgcaac agagtgggga actagccaag caaatggaga tggtggtcct   1560
tactttgatg aagcagatgt atggattgag tttttaaatg aaaacaacat tagctgggct   1620
aactggtctt taacgaataa aaatgaagta tctggtgcat ttacaccatt cgagttaggt   1680
aagtctaacg caacaagtct tgacccaggg ccagaccaag tatgggtacc agaagagtta   1740
agtctttctg gagaatatgt acgtgctcgt attaaaggtg tgaactatga gccaatcgac   1800
cgtacaaaat acacgaaagt actttgggac tttaatgatg gaacgaagca aggatttgga   1860
gtgaatggag attctccagt tgaagatgta gttattgaga atgaagcggg cgctttaaaa   1920 cttttcaggat tagatgcaag taatgatgtt tctgaaggta attactgggc taatgctcgt   1980 cttttctgccg acggttgggg aaaaagtgtt gatattttag gtgctgaaaa acttactatg   2040
gatgtgattg ttgatgagcc gaccacggta tcaattgctg caattccaca agggccatca   2100
gccaattggg ttaatccaaa tcgtgcaatt aaggttgagc caactaattt cgtaccgtta   2160
ggagataagt ttaaagcgga attaactata acttcagctg actctccatc gttagaagct   2220
attgcgatgc atgctgaaaa taacaacatc aacaacatca ttcttttttgt aggaactgaa   2280 ggtgctgatg ttatctattt agataacatt aaagtaattg gaacagaagt tgaaattcca   2340
gttgttcatg atccaaaagg agaagctgtt cttccttctg tttttgaaga cggtacacgt   2400
caaggttggg actgggctgg agagtctggt gtgaaaacag ctttaacaat tgaagaagca   2460
aacggttcta acgcgttatc atgggaattt ggatacccag aagtaaaacc tagtgataac   2520
tgggcaacag ctccacgttt agatttctgg aaatctgact tggttcgcgg tgaaaatgat   2580
tatgtaactt ttgatttcta tctagatcca gttcgtgcaa cagaaggcgc aatgaatatc   2640
aatttagtat tccagccacc tactaacggg tattgggtac aagcaccaaa aacgtatacg   2700
attaactttg atgaattaga ggaagcgaat caagtaaatg gtttatatca ctatgaagtg   2760
aaaattaacg taagagatat tacaaacatt caagatgaca cgttactacg taacatgatg   2820 atcattttg cagatgtaga aagtgacttt gcagggagag tctttgtaga taatgttcgt   2880
tttgaggggg ctgctactac tgagccggtt gaaccagagc cagttgatcc tggcgaagag   2940
acgccgcctg tcgatgagaa ggaagcgaaa aagaacaaa agaagcaga gaaagaagag   3000 aagaagcag taaaagaaga aaagaaagaa gctaagaag aaagaaagc aatcaaaaat   3060 gaggctacga aaaataatc taataaaacta gttataggt tatctaaagg tctgatgcag   3120
atcttttaga taaccttttt ttgcataact ggacatagaa tggttattaa agaaagcaag   3180
gtgtttatac gatattaaaa aggtagcgat tttaaattga aacctttaat aatgtcttgt   3240
```

```
gatagaatga tgaagtaatt taagaggggg aaacgaagtg aaaacggaaa tttctagtag    3300
aagaaaaaca gaccaagaaa tactgcaagc tt                                  3332
```

<210> SEQ ID NO 6
<211> LENGTH: 793
<212> TYPE: PRT
<213> ORGANISM: Baccillus sp. KSM-64

<400> SEQUENCE: 6

```
Ala Glu Gly Asn Thr Arg Glu Asp Asn Phe Lys His Leu Leu Gly Asn
1               5                   10                  15

Asp Asn Val Lys Arg Pro Ser Glu Ala Gly Ala Leu Gln Leu Gln Glu
            20                  25                  30

Val Asp Gly Gln Met Thr Leu Val Asp Gln His Gly Glu Lys Ile Gln
        35                  40                  45

Leu Arg Gly Met Ser Thr His Gly Leu Gln Trp Phe Pro Glu Ile Leu
    50                  55                  60

Asn Asp Asn Ala Tyr Lys Ala Leu Ala Asn Asp Trp Glu Ser Asn Met
65                  70                  75                  80

Ile Arg Leu Ala Met Tyr Val Gly Glu Asn Gly Tyr Ala Ser Asn Pro
                85                  90                  95

Glu Leu Ile Lys Ser Arg Val Ile Lys Gly Ile Asp Leu Ala Ile Glu
            100                 105                 110

Asn Asp Met Tyr Val Ile Val Asp Trp His Val His Ala Pro Gly Asp
        115                 120                 125

Pro Arg Asp Pro Val Tyr Ala Gly Ala Glu Asp Phe Phe Arg Asp Ile
    130                 135                 140

Ala Ala Leu Tyr Pro Asn Asn Pro His Ile Ile Tyr Glu Leu Ala Asn
145                 150                 155                 160

Glu Pro Ser Ser Asn Asn Asn Gly Gly Ala Gly Ile Pro Asn Asn Glu
                165                 170                 175

Glu Gly Trp Asn Ala Val Lys Glu Tyr Ala Asp Pro Ile Val Glu Met
            180                 185                 190

Leu Arg Asp Ser Gly Asn Ala Asp Asp Asn Ile Ile Ile Val Gly Ser
        195                 200                 205

Pro Asn Trp Ser Gln Arg Pro Asp Leu Ala Ala Asp Asn Pro Ile Asp
    210                 215                 220

Asp His His Thr Met Tyr Thr Val His Phe Tyr Thr Gly Ser His Ala
225                 230                 235                 240

Ala Ser Thr Glu Ser Tyr Pro Pro Glu Thr Pro Asn Ser Glu Arg Gly
                245                 250                 255

Asn Val Met Ser Asn Thr Arg Tyr Ala Leu Glu Asn Gly Val Ala Val
            260                 265                 270

Phe Ala Thr Glu Trp Gly Thr Ser Gln Ala Asn Gly Asp Gly Gly Pro
        275                 280                 285

Tyr Phe Asp Glu Ala Asp Val Trp Ile Glu Phe Leu Asn Glu Asn Asn
    290                 295                 300

Ile Ser Trp Ala Asn Trp Ser Leu Thr Asn Lys Asn Glu Val Ser Gly
305                 310                 315                 320

Ala Phe Thr Pro Phe Glu Leu Gly Lys Ser Asn Ala Thr Ser Leu Asp
                325                 330                 335

Pro Gly Pro Asp Gln Val Trp Val Pro Glu Glu Leu Ser Leu Ser Gly
            340                 345                 350

Glu Tyr Val Arg Ala Arg Ile Lys Gly Val Asn Tyr Glu Pro Ile Asp
        355                 360                 365
```

-continued

```
Arg Thr Lys Tyr Thr Lys Val Leu Trp Asp Phe Asn Asp Gly Thr Lys
    370             375             380
Gln Gly Phe Gly Val Asn Gly Asp Ser Pro Val Glu Asp Val Val Ile
385             390             395             400
Glu Asn Glu Ala Gly Ala Leu Lys Leu Ser Gly Leu Asp Ala Ser Asn
                405             410             415
Asp Val Ser Glu Gly Asn Tyr Trp Ala Asn Ala Arg Leu Ser Ala Asp
            420             425             430
Gly Trp Gly Lys Ser Val Asp Ile Leu Gly Ala Glu Lys Leu Thr Met
        435             440             445
Asp Val Ile Val Asp Glu Pro Thr Thr Val Ser Ile Ala Ala Ile Pro
    450             455             460
Gln Gly Pro Ser Ala Asn Trp Val Asn Pro Asn Arg Ala Ile Lys Val
465             470             475             480
Glu Pro Thr Asn Phe Val Pro Leu Gly Asp Lys Phe Lys Ala Glu Leu
                485             490             495
Thr Ile Thr Ser Ala Asp Ser Pro Ser Leu Glu Ala Ile Ala Met His
            500             505             510
Ala Glu Asn Asn Ile Asn Asn Ile Ile Leu Phe Val Gly Thr Glu
        515             520             525
Gly Ala Asp Val Ile Tyr Leu Asp Asn Ile Lys Val Ile Gly Thr Glu
    530             535             540
Val Glu Ile Pro Val Val His Asp Pro Lys Gly Glu Ala Val Leu Pro
545             550             555             560
Ser Val Phe Glu Asp Gly Thr Arg Gln Gly Trp Asp Trp Ala Gly Glu
                565             570             575
Ser Gly Val Lys Thr Ala Leu Thr Ile Glu Glu Ala Asn Gly Ser Asn
            580             585             590
Ala Leu Ser Trp Glu Phe Gly Tyr Pro Glu Val Lys Pro Ser Asp Asn
        595             600             605
Trp Ala Thr Ala Pro Arg Leu Asp Phe Trp Lys Ser Asp Leu Val Arg
    610             615             620
Gly Glu Asn Asp Tyr Val Thr Phe Asp Phe Tyr Leu Asp Pro Val Arg
625             630             635             640
Ala Thr Glu Gly Ala Met Asn Ile Asn Leu Val Phe Gln Pro Pro Thr
                645             650             655
Asn Gly Tyr Trp Val Gln Ala Pro Lys Thr Tyr Thr Ile Asn Phe Asp
            660             665             670
Glu Leu Glu Glu Ala Asn Gln Val Asn Gly Leu Tyr His Tyr Glu Val
        675             680             685
Lys Ile Asn Val Arg Asp Ile Thr Asn Ile Gln Asp Asp Thr Leu Leu
    690             695             700
Arg Asn Met Met Ile Ile Phe Ala Asp Val Glu Ser Asp Phe Ala Gly
705             710             715             720
Arg Val Phe Val Asp Asn Val Arg Phe Glu Gly Ala Ala Thr Thr Glu
                725             730             735
Pro Val Glu Pro Glu Pro Val Asp Pro Gly Glu Thr Pro Pro Val
            740             745             750
Asp Glu Lys Glu Ala Lys Lys Glu Gln Lys Glu Ala Glu Lys Glu Glu
        755             760             765
Lys Glu Ala Val Lys Glu Glu Lys Lys Glu Ala Lys Glu Glu Lys Lys
    770             775             780
Ala Ile Lys Asn Glu Ala Thr Lys Lys
785             790
```

-continued

```
<210> SEQ ID NO 7
<211> LENGTH: 572
<212> TYPE: DNA
<213> ORGANISM: Bacillus sp. KSM-S237

<400> SEQUENCE: 7
gatttgccga tgcaacaggc ttatatttag aggaaatttc tttttaaatt gaatacggaa      60
taaaatcagg taaacaggtc ctgattttat tttttgagt tttttagaga actgaagatt     120 gaataaaag tagaagacaa aggacataag aaaattgcat tagttttaat tatagaaaac     180
gcctttttat aattatttat acctagaacg aaaatactgt ttcgaaagcg gtttactata     240
aaaccttata ttccggctct tttttaaaac aggggggtaaa aattcactct agtattctaa    300
tttcaacatg ctataataaa tttgtaagac gcaatatgca tctcttttt tacgatatat     360 gtaagcggtt aaccttgtgc tatatgccga tttaggaagg ggggtagaat atttcaagta    420
gtaataacat acaatactta taagttgttg agaagcagga gagcatctgg gttactcaca    480
agttttttta aaactttaac gaaagcactt tcggtaatgc ttatgaattt agctatttga    540
ttcaattact ttaaaaatat ttaggaggta at                                   572

<210> SEQ ID NO 8
<211> LENGTH: 609
<212> TYPE: DNA
<213> ORGANISM: Bacillus sp. KSM-64

<400> SEQUENCE: 8
agtacttacc attttagagt caaagatag aagccaagca ggatttgccg atgcaaccgg       60
cttatattta gagggaattt cttttaaat tgaatacgga ataaaatcag gtaaacaggt     120
cctgatttta ttttttgaa ttttttgag aactaaagat tgaaatagaa gtagaagaca      180
acggacataa gaaaattgta ttagttttaa ttatagaaaa cgcttttcta attattttta    240
tacctagaac gaaaatactg tttcgaaagc ggtttactat aaaaacttat attccggctc    300 ttttttaaa caggggggtga aaattcactc tagtattcta atttcaacat gctataataa    360
atttgtaaga cgcaatatac atcttttttt tatgatattt gtaagcggtt aaccttgtgc    420
tatatgccga tttaggaagg gggtagaata tttcaagtag taataacata caatacttat    480
aagttgttga gaagcaggag agaatctggg ttactcacaa gttttttaaa acattatcga    540
aagcactttc ggttatgctt atgaatttag ctatttgatt caattacttt aataattta    600 ggaggtaat                                                            609

<210> SEQ ID NO 9
<211> LENGTH: 37
<212> TYPE: DNA
<213> ORGANISM: Artificial sequence
<220> FEATURE:
<223> OTHER INFORMATION: Oligonucleotide as PCR primer designed from
      nucleotide sequence of Bacillus sp. KSM-S237 gene for cellulase;
      the sequece with a insertion of the BamHI restriction site at the
      5'-end

<400> SEQUENCE: 9
ttgcggatcc aacaggctta tatttagagg aaatttc                               37

<210> SEQ ID NO 10
<211> LENGTH: 40
<212> TYPE: DNA
<213> ORGANISM: Artificial sequence
```

```
<220> FEATURE:
<223> OTHER INFORMATION: Oligonucleotide as PCR primer designed from
      nucleotide sequence of Bacillus sp. KSM-S237 gene for cellulase;
      the sequence containing eight nucleotides substitution for SigmaE
      recognition

<400> SEQUENCE: 10
gtatgttatt actacttgaa atattctacc cccttccta                          40

<210> SEQ ID NO 11
<211> LENGTH: 39
<212> TYPE: DNA
<213> ORGANISM: Artificial sequence
<220> FEATURE:
<223> OTHER INFORMATION: Oligonucleotide as PCR primer designed from
      nucleotide sequence of Bacillus sp. KSM-S237 gene for cellulase;
      the sequence containing eight nucleotides substitution for SigmaE
      recognition

<400> SEQUENCE: 11
atatttcaag tagtaataac atacaatact tataagttg                          39

<210> SEQ ID NO 12
<211> LENGTH: 20
<212> TYPE: DNA
<213> ORGANISM: Artificial sequence
<220> FEATURE:
<223> OTHER INFORMATION: Oligonucleotide as PCR primer designed from
      nucleotide sequence of Bacillus sp. KSM-S237 gene for cellulase

<400> SEQUENCE: 12
tcgctaccct tttattatcg                                               20

<210> SEQ ID NO 13
<211> LENGTH: 1795
<212> TYPE: DNA
<213> ORGANISM: Bacillus sp. KSM-K38

<400> SEQUENCE: 13
caggccagcc aaagtagcca ccaactaagt aacatcgatt caggataaaa gtatgcgaaa    60
cgatgcgcaa aactgcgcaa ctactagcac tcttcaggga ctaaaccacc ttttttccaa   120
aaatgacatc atataaacaa atttgtctac caatcactat ttaaagctgt ttatgatata   180
tgtaagcgtt atcattaaaa ggaggtattt gatgagaaga tgggtagtag caatgttggc   240
agtgttattt ttatttcctt cggtagtagt tgcagatgga ttgaacggta cgatgatgca   300
gtattatgag tggcatttgg aaaacgacgg gcagcattgg aatcggttgc acgatgatgc   360
cgcagctttg agtgatgctg gtattacagc tatttggatt ccgccagcct acaaaggtaa   420
tagtcaggcg gatgttgggt acggtgcata cgatctttat gatttaggag agttcaatca   480
aaagggtact gttcgaacga aatacggaac taaggcacag cttgaacgag ctattgggtc   540
ccttaaatct aatgatatca atgtatacgg agatgtcgtg atgaatcata aaatgggagc   600
tgattttacg gaggcagtgc aagctgttca agtaaatcca acgaatcgtt ggcaggatat   660
ttcaggtgcc tacacgattg atgcgtggac gggtttcgac ttttcagggc gtaacaacgc   720
ctattcagat tttaagtgga gatggttcca ttttaatggt gttgactggg atcagcgcta   780
tcaagaaaat catattttcc gctttgcaaa tacgaactgg aactggcgag tggatgaaga   840
gaacggtaat tatgattacc tgttaggatc gaatatcgac tttagtcatc cagaagtaca   900
agatgagttg aaggattggg gtagctggtt taccgatgag ttagatttgg atggttatcg   960
tttagatgct attaaacata ttccattctg gtatacatct gattgggttc ggcatcagcg  1020
```

-continued

```
caacgaagca gatcaagatt tatttgtcgt agggggaatat tggaaggatg acgtaggtgc    1080
tctcgaattt tatttagatg aaatgaattg ggagatgtct ctattcgatg ttccacttaa    1140
ttataatttt taccgggctt cacaacaagg tggaagctat gatatgcgta atattttacg    1200
aggatcttta gtagaagcgc atccgatgca tgcagttacg tttgttgata atcatgatac    1260
tcagccaggg gagtcattag agtcatgggt tgctgattgg tttaagccac ttgcttatgc    1320
gacaattttg acgcgtgaag gtggttatcc aaatgtattt tacggtgatt actatgggat    1380
tcctaacgat aacatttcag ctaaaaaaga tatgattgat gagctgcttg atgcacgtca    1440
aaattacgca tatggcacgc agcatgacta ttttgatcat tgggatgttg taggatggac    1500
tagggaagga tcttcctcca gacctaattc aggccttgcg actattatgt cgaatggacc    1560
tggtggttcc aagtggatgt atgtaggacg tcagaatgca ggacaaacat ggacagattt    1620
aactggtaat aacggagcgt ccgttacaat taatggcgat ggatggggcg aattctttac    1680
gaatggagga tctgtatccg tgtacgtgaa ccaataacaa aaagccttga gaagggattc    1740
ctccctaact caaggctttc tttatgtcgc ttagctttac gcttctacga ctttg        1795
```

<210> SEQ ID NO 14
<211> LENGTH: 480
<212> TYPE: PRT
<213> ORGANISM: Bacillus sp. KSM-K38

<400> SEQUENCE: 14

```
Asp Gly Leu Asn Gly Thr Met Met Gln Tyr Tyr Glu Trp His Leu Glu
1               5                   10                  15

Asn Asp Gly Gln His Trp Asn Arg Leu His Asp Asp Ala Ala Ala Leu
            20                  25                  30

Ser Asp Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
        115                 120                 125

Ile Ser Gly Ala Tyr Thr Ile Asp Ala Trp Thr Gly Phe Asp Phe Ser
    130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240
```

```
Thr Ser Asp Trp Val Arg His Gln Arg Asn Glu Ala Asp Gln Asp Leu
            245                 250                 255

Phe Val Val Gly Glu Tyr Trp Lys Asp Val Gly Ala Leu Glu Phe
        260                 265                 270

Tyr Leu Asp Glu Met Asn Trp Glu Met Ser Leu Phe Asp Val Pro Leu
            275                 280                 285

Asn Tyr Asn Phe Tyr Arg Ala Ser Gln Gln Gly Gly Ser Tyr Asp Met
        290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
            325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
            355                 360                 365

Ile Pro Asn Asp Asn Ile Ser Ala Lys Lys Asp Met Ile Asp Glu Leu
        370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Arg
            405                 410                 415

Pro Asn Ser Gly Leu Ala Thr Ile Met Ser Asn Gly Pro Gly Ser
            420                 425                 430

Lys Trp Met Tyr Val Gly Arg Gln Asn Ala Gly Gln Thr Trp Thr Asp
            435                 440                 445

Leu Thr Gly Asn Asn Gly Ala Ser Val Thr Ile Asn Gly Asp Gly Trp
        450                 455                 460

Gly Glu Phe Phe Thr Asn Gly Gly Ser Val Ser Val Tyr Val Asn Gln
465                 470                 475                 480

<210> SEQ ID NO 15
<211> LENGTH: 25
<212> TYPE: DNA
<213> ORGANISM: Artificial sequence
<220> FEATURE:
<223> OTHER INFORMATION: Oligonucleotide as PCR primer designed from
      nucleotide sequence of Bacillus sp. KSM-S237 gene for cellulase;
      the sequece with a insertion of the BamHI restriction site at the
      5'-end

<400> SEQUENCE: 15
cccggatcca acaggcttat attta                                             25

<210> SEQ ID NO 16
<211> LENGTH: 29
<212> TYPE: DNA
<213> ORGANISM: Artificial sequence
<220> FEATURE:
<223> OTHER INFORMATION: Oligonucleotide as PCR primer; its 3'-portion
      designed from nucleotide sequence of Bacillus sp. KSM-S237 gene
      for cellulase and its 5'-portion designed from nucleotide sequence
      of Bacillus sp. KSM-K38 gene for amylase

<400> SEQUENCE: 16
ttcaatccat ctgctgcaag agctgccgg                                         29

<210> SEQ ID NO 17
<211> LENGTH: 30
<212> TYPE: DNA
<213> ORGANISM: Artificial sequence
```

```
<220> FEATURE:
<223> OTHER INFORMATION: Oligonucleotide as PCR primer; its 3'-portion
      designed from nucleotide sequence of Bacillus sp. KSM-K38 gene for
      amylase and its 5'-portion designed from nucleotide sequence of
      Bacillus sp. KSM-S237 gene for cellulase

<400> SEQUENCE: 17
gctcttgcag cagatggatt gaacggtacg                                    30

<210> SEQ ID NO 18
<211> LENGTH: 30
<212> TYPE: DNA
<213> ORGANISM: Artificial sequence
<220> FEATURE:
<223> OTHER INFORMATION: Oligonucleotide as PCR primer designed from
      nucleotide sequence of Bacillus sp. KSM-K38 gene for amylase; the
      sequece with a insertion of the XbaI restriction site at the
      5'-end

<400> SEQUENCE: 18
ttggtctaga ccccaagctt caaagtcgta                                    30

<210> SEQ ID NO 19
<211> LENGTH: 27
<212> TYPE: DNA
<213> ORGANISM: Artificial sequence
<220> FEATURE:
<223> OTHER INFORMATION: A promoter sequence recognized by SigE

<400> SEQUENCE: 19
atatttcaag tagtaataac atacaat                                       27

<210> SEQ ID NO 20
<211> LENGTH: 27
<212> TYPE: DNA
<213> ORGANISM: Artificial sequence
<220> FEATURE:
<223> OTHER INFORMATION: Original sequence in an alkaline cellulase gene

<400> SEQUENCE: 20
ttgagtcaag tagtaataat atagata                                       27
```

The invention claimed is:

1. A promoter region comprising a consensus sequence recognized by SigA and a consensus sequence recognized by SigE, which is produced by modifying a nucleotide sequence including a promoter recognized by SigA and bases in the vicinity thereof, to further include said consensus sequence recognized by SigE, with said consensus sequence recognized by SigA being maintained,
   wherein the consensus sequence recognized by SigE is a nucleotide sequence comprising a −35 region represented by ATAHTT and a −10 region represented by CATAYAHT, wherein H denotes A, C, or T and Y denotes C or T, which is linked to a site 13 or 14 nucleotides downstream from the −35 region,
   wherein the consensus sequence recognized by SigA is a nucleotide sequence comprising a −35 region represented by TTGACA and a −10 region represented by TGNTATAAT, which is linked to a site 14 nucleotides downstream from the −35 region, wherein N represents A, G, C, or T, and
   wherein said nucleotide sequence including a promoter recognized by SigA and bases in the vicinity thereof comprises a nucleotide sequence ranging from base Nos. 92 to 552 in SEQ ID NO: 1, a nucleotide sequence ranging from base Nos. 133 to 589 in SEQ ID NO: 2, or a nucleotide sequence having a homology of 80% or more to either of these nucleotide sequences.

2. The promoter DNA according to claim 1, wherein said nucleotide sequence including a promoter recognized by SigA and bases in the vicinity thereof comprises a nucleotide sequence ranging from base Nos. 92 to 552 in SEQ ID NO: 1, a nucleotide sequence ranging from base Nos. 133 to 589 in SEQ ID NO: 2, or a nucleotide sequence having a homology of 90% or more to either of these nucleotide sequences.

3. The promoter DNA according to claim 1, wherein the nucleotide sequence having a promoter recognized by SigA and bases in the vicinity of the promoter has a size of 610 bp or less.

4. A promoter DNA which is produced by ligating two or more promoter DNAs according to claim 1.

5. An expression vector which has the promoter DNA according to claim 1.

6. A recombinant microorganism which has the expression vector according to claim 5.

7. A recombinant microorganism which has the promoter DNA according to claim 1 on the genome.

8. A method for producing a protein or a polypeptide, comprising culturing the recombinant microorganism according to claim 6.

9. The method according to claim 8, wherein the protein is cellulase or amylase.

10. The method according to claim 9, wherein the cellulase is an alkaline cellulase which has an amino acid sequence of SEQ ID NO: 4, or a protein which has a homology of 70% or more to the amino acid sequence and alkaline cellulase activity.

11. The method according to claim 9, wherein the amylase is an alkaline amylase which has an amino acid sequence of SEQ ID NO: 14, or a protein which has a homology of 70% or more to the amino acid sequence and alkaline amylase activity.

12. A method for constructing a promoter DNA, comprising modifying a nucleotide sequence having a promoter recognized by SigA and having a nucleotide present in the vicinity of the promoter so as to be recognized by SigA and SigE, wherein said promoter DNA is a promoter DNA according to claim 1.

13. A method for producing a protein or a polypeptide, comprising culturing the recombinant microorganism according to claim 7.

14. The method according to claim 13, wherein the protein is cellulase or amylase.

15. The method according to claim 14, wherein the cellulase is an alkaline cellulase which has an amino acid sequence of SEQ ID NO: 4, or a protein which has a homology of 70% or more to the amino acid sequence and alkaline cellulase activity.

16. The method according to claim 14, wherein the amylase is an alkaline amylase which has an amino acid sequence of SEQ ID NO: 14, or a protein which has a homology of 70% or more to the amino acid sequence and alkaline amylase activity.

17. The promoter DNA according to claim 1, wherein the consensus sequence recognized by SigE is a nucleotide sequence comprising a −35 region represented by ATATTT and a −10 region represented by CATACAAT which is linked to a site 13 or 14 nucleotides downstream from the −35 region.

18. The promoter DNA according to claim 1, wherein the consensus sequence recognized by SigE is a nucleotide sequence represented by ATATTTCAAGTAGTAATAACATACAAT (SEQ ID NO: 19).

19. The promoter DNA according to claim 1, wherein said promoter DNA comprises the nucleotide sequence of SEQ ID NO: 7.

20. The promoter DNA according to claim 4, wherein said promoter DNA comprises the nucleotide sequence of SEQ ID NO: 8.

21. The promoter DNA according to claim 1, wherein said promoter nucleotide sequence including a promoter recognized by SigA and bases in the vicinity thereof comprises a nucleotide sequence ranging from base Nos. 92 to 552 in SEQ ID NO: 1, a nucleotide sequence ranging from base Nos. 133 to 589 in SEQ ID NO: 2, or a nucleotide sequence having a homology of 95% or more to either of these nucleotide sequences.

22. The promoter DNA according to claim 1, wherein said nucleotide sequence including a promoter recognized by SigA and bases in the vicinity thereof comprises a nucleotide sequence ranging from base Nos. 92 to 552 in SEQ ID NO: 1, a nucleotide sequence ranging from base Nos. 133 to 589 in SEQ ID NO: 2, or a nucleotide sequence having a homology of 98% or more to either of these nucleotide sequences.

23. The method according to claim 10, wherein the cellulase is an alkaline cellulase having an amino acid sequence that has 80% homology or more to the amino acid sequence of SEQ ID NO: 4 and having alkaline cellulase activity.

24. The method according to claim 10, wherein the cellulase is an alkaline cellulase having an amino acid sequence that has 90% homology or more to the amino acid sequence of SEQ ID NO: 4 and having alkaline cellulase activity.

25. The method according to claim 10, wherein the cellulase is an alkaline cellulase having an amino acid sequence that has 95% homology or more to the amino acid sequence of SEQ ID NO: 4 and having alkaline cellulase activity.

26. The method according to claim 11, wherein the amylase is an alkaline amylase having an amino acid sequence that has 80% homology or more to the amino acid sequence of SEQ ID NO: 14 and having alkaline amylase activity.

27. The method according to claim 11, wherein the amylase is an alkaline amylase having an amino acid sequence that has 90% homology or more to the amino acid sequence of SEQ ID NO: 14 and having alkaline amylase activity.

28. The method according to claim 11, wherein the amylase is an alkaline amylase having an amino acid sequence that has 95% homology or more to the amino acid sequence of SEQ ID NO: 14 and having alkaline amylase activity.

29. The method according to claim 15, wherein the cellulase is an alkaline cellulase having an amino acid sequence that has 80% homology or more to the amino acid sequence of SEQ ID NO: 4 and having alkaline cellulase activity.

30. The method according to claim 15, wherein the cellulase is an alkaline cellulase having an amino acid sequence that has 90% homology or more to the amino acid sequence of SEQ ID NO: 4 and having alkaline cellulase activity.

31. The method according to claim 15, wherein the cellulase is an alkaline cellulase having an amino acid sequence that has 95% homology or more to the amino acid sequence of SEQ ID NO: 4 and having alkaline cellulase activity.

32. The method according to claim 16, wherein the amylase is an alkaline amylase having an amino acid sequence that has 80% homology or more to the amino acid sequence of SEQ ID NO: 14 and having alkaline amylase activity.

33. The method according to claim 16, wherein the amylase is an alkaline amylase having an amino acid sequence that has 90% homology or more to the amino acid sequence of SEQ ID NO: 14 and having alkaline amylase activity.

34. The method according to claim 16, wherein the amylase is an alkaline amylase having an amino acid sequence that has 95% homology or more to the amino acid sequence of SEQ ID NO: 14 and having alkaline amylase activity.

* * * * *